United States Patent [19]

Garvey et al.

[11] Patent Number: 4,740,528
[45] Date of Patent: Apr. 26, 1988

[54] SUPERWICKING CROSSLINKED POLYURETHANE FOAM COMPOSITION CONTAINING AMINO ACID

[75] Inventors: Chad E. Garvey, Ball Ground; Gerard J. F. Ring, Woodstock, both of Ga.

[73] Assignee: Kimberly-Clark Corporation, Neenah, Wis.

[21] Appl. No.: 888,550

[22] Filed: Jul. 18, 1986

[51] Int. Cl.$^4$ ............... C08J 9/00; C08K 9/00; C08G 18/00

[52] U.S. Cl. .................... 521/128; 521/157; 604/369

[58] Field of Search ............... 521/128, 157

[56] References Cited

U.S. PATENT DOCUMENTS 4,127,516 11/1978 Larsen et al. ............ 521/137
4,182,827 1/1980 Jones et al. ............ 528/61

Primary Examiner—Harold D. Anderson
Assistant Examiner—Dennis R. Daley
Attorney, Agent, or Firm—William E. Maycock

[57] ABSTRACT

An absorbent superwicking crosslinked polyurethane foam composition, into which is incorporated an effective amount of at least one amino acid, a one percent by weight aqueous solution of which has a pH of no more than about 8. The amino acid contains one amino group and at least one carboxylic acid group. A method for preparing such compositions also is described.

The polyurethane foam composition is useful as a sponge and in the manufacture of such absorbent composite structures as disposable diapers, incontinent products, disposable bibs, feminine care products such as tampons and napkins, and the like.

20 Claims, 9 Drawing Sheets

FIGURE 8
CAPACITY VS. TIME
SAMPLE G

SUPERWICKING CROSSLINKED POLYURETHANE FOAM COMPOSITION CONTAINING AMINO ACID

BACKGROUND OF THE INVENTION

The present invention relates to crosslinked polyurethane foam compositions. More particularly, the present invention relates to crosslinked polyurethane foam compositions having greatly enhanced wicking capabilities; i.e.; superwicking crosslinked polyurethane foam compositions.

Polyurethane foams are, of course, well known to those having ordinary skill in the art. Indeed, a voluminous body of literature has accumulated over the years as researchers explored combinations of starting materials and correlated starting materials with foam properties. Moreover, numerous efforts have been made to either modify the physical properties of polyurethane foams or to prepare specialized polyurethane foams having unique properties.

Among the properties of particular interest is the property of increased water absorbence. Polymers having this property often are referred to as hydrogels or superabsorbents.

The nature and utility of superabsorbents is illustrated by U.S. Pat. No. 4,449,997, although it will be appreciated by those having ordinary skill in the art that numerous other references also could be cited. According to this reference, an apparently desirable feature of a superabsorbent is the presence of acrylate or methacrylate groups which can be salts, amides, esters, or the free acids.

As a practical matter, many hydrogels are based on acrylate and methacrylate polymers and copolymers. See, by way of example only, U.S. Pat. Nos. 2,976,576, 3,220,960, 3,993,616, 4,154,898, 4,167,464, 4,192,727, 4,192,827, and 4,529,739. The last-cited patent is of particular interest since the disclosed water-absorbent polymers are foamed. Other hydrogels are based on starch or a modified starch, as shown by U.S. Pat. Nos. 4,069,177, 4,076,663, 4,115,332, and 4,117,222. Still other hydrogels are based on poly(oxyalkylene) glycols; see, e.g., U.S. Pat. No. 3,783,872. Hydrogels prepared from hydrolyzed crosslinked polyacrylamides and crosslinked sulfonated polystyrenes are described in U.S. Pat. No. 4,235,237. Finally, polymers based on maleic anhydride (or similar compounds) have been described in U.S. Pat. Nos. 2,988,539, 3,393,168, 3,514,419, 3,557,067, and 4,401,793. U.S. Pat. No. 3,900,378 is of interest since it describes hydrogels from radiation crosslinked blends of hydrophilic polymers and fillers, many of the polymers being those described in the foregoing patents.

Polyurethane hydrogels are, of course, known and frequently are based on the reaction of a poly(alkyleneoxy) polyol with a diisocyanate. Such reaction has been studied at length. Exemplary of such polyurethane hydrogels are the references summarized below.

U.S. Pat. No. 3,939,105 describes microporous polyurethane hydrogels. The hydrogels are the reaction products of a poly(alkyleneoxy) polyol having an average molecular weight of up to about 25,000 and organic diisocyanate which have been lightly crosslinked with water or an organic amine. In practice, the polyol is reacted with the diisocyanate to give an isocyanate-capped polyol. Before the isocyanate-capped polyol is crosslinked, a liquid nonsolvent is added thereto in an amount which will not result in precipitation. It is the addition of the nonsolvent which results in the production of the microporous hydrogel. The nonsolvent typically is an aliphatic hydrocarbon or a dialkyl ether.

The disclosure of U.S. Pat. No. 3,939,123 is similar to that of the foregoing patent, except that in the present patent a nonsolvent is not employed.

In a variation of the procedures disclosed in the two preceding patents, U.S. Pat. No. 3,940,542 describes the extrusion of the isocyanate-capped poly(alkyleneoxy) polyol of such preceding patents into a coagulant or crosslinking bath containing water or an organic polyamine as a crosslinking agent to produce water swellable, lightly crosslinked hydrogel polymer tapes or fibers. U.S. Pat. No. 4,209,605 describes another variation in which hydrogels are produced by charging preselected feeds containing the poly(alkyleneoxy) polyol, diisocyanate, and catalyst to a reaction zone, extruding the resulting high viscosity polymer through a suitable die, and allowing crosslinking to take place by exposure to atmospheric humidity.

U.S. Pat. No. 4,182,827 describes a method of increasing the wetting rates of the hydrogels disclosed in the above three patents. The wetting rates are enhanced by treating the surface of the solid hydrogel with certain ketones, alcohols, organic amines, aromatic hydrocarbons, or aqueous alkali metal hydroxide solutions.

It appears to be generally known that the best superabsorbent polymers are polyelectrolytes. That is, such superabsorbents contain a plurality of ionic groups. The preferred ionic groups are salts of carboxylic acids. Examples of carboxylate-containing polyurethanes and polyurethane hydrogels are noted below.

U.S. Pat. No. 3,412,054 describes water-dilutable polyurethanes which are useful as surface coatings and printing inks. Such polyurethanes contain carboxylic acid groups which can be neutralized with ammonia or an amine. The carboxylic acid groups are provided by incorporating into the polyurethane a 2,2-bis(hdroxymethyl)-substituted carboxylic acid. Examples of suitable acids include 2,2-bis(hydroxymethyl)acetic acid, 2,2,2-tris(hydroxymethyl)acetic acid, 2,2-bis(hydromethyl)propionic acid, 2,2-bis(hydroxymethyl)butyric acid,. 2,2-bis (hydroxymethyl) pentanoic acid, and the like. The polyurethanes are prepared by known techniques, such as adding organic diisocyanate to a mixture of a suitable carboxylic acid and a polyol polyurethane precursor.

U.S. Pat. No. 4,156,066 discloses polyurethanes characterized by lactone groups and hydroxy groups in the polymer backbone. The polyurethanes are prepared by reacting an organic polyisocyanate with a poly(alkyleneoxy) polyol and a polyfunctional lactone having excess hydroxy groups. The free hydroxy groups which are present in the formed polyurethane are available for crosslinking the polymer. See also U.S. Pat. No. 4,156,067. The lactone groups can be hydrolyzed to form free carboxylic acid groups or carboxylate groups, as taught by U.S. Pat. No. 4,255,550. The hydrolyzed polyurethane in turn can be reacted with an organic chloride in the presence of a strong base, followed by treatment with hydrochloric acid to give a polyurethane containing quaternary ammonium chloride groups. See, e.g., U.S. Pat. No. 4,451,635.

U.S. Pat. No. 3,928,299 describes the reaction of a hydroxy group-containing polymer with an unsaturated isocyanate. Suitable hydroxy group-containing polymers can be obtained by the polymerization of hydroxyalkyl esters of acrylic acid or alpha-alkyl-substituted acrylic acids or by the copolymerization of these compounds with other vinyl or vinylidene compounds. Suitable hydroxyalkyl esters are the monoesters of the foregoing acids with ethylene glycol, propylene glycol, propane-1,3-diol, butanediol, diethylene glycol, and higher polyethylene glycols. Such polymers also can be polyesters of polybasic aliphatic or aromatic carboxylic acids with polyhydric alcohols, polyurethanes which contain hydroxy groups, or epoxy resins which contain hydroxy groups. The resulting polymers are crosslinkable by vinyl polymerization and are useful for the preparation of coatings and molded products. Foams, especially polyurethane foams, are not mentioned. See also U.S. Pat. No. 4,210,713.

Disclosures similar to that of the above patent are found in U.S. Pat. Nos. 3,871,908, 3,856,830 3,954,714, and 4,082,710.

U.S. Pat. No. 4,131,602 describes radiation-curable acrylated polyurethane coating compositions. The compositions are prepared by reacting an isocyanate-terminated urethane intermediate with an amount of a hydroxyalkyl, hydroxycycloalkyl, or hydroxyaryl ester of acrylic acid or methacrylic acid which is sufficient to react with at least 80 percent of the isocyanate groups of the urethane intermediate. The urethane intermediate is the reaction product of an organic diisocyanate, an organic triol or tetraol which is either a polyester or a polyether, and an organic diol which is either a polyester or a polyether. The diisocyanate is used in an equivalent excess to the other two components. In addition, when the triol or tetraol is a polyester, the diol must be a polyether, and when the triol or tetraol is a polyether, the diol must be a polyester.

U.S. Pat. No. 4,153,778 describes acrylyl-capped urethane oligomers which readily cure by thermal or radiation means and are useful as coatings, binders, and adhesives. The oligomers are the reaction products of a poly(oxytetramethylene) diol or a polycaprolactone polyol, an organic diisocyanate, a di- or tri-methylol carboxylic acid, and an acrylyl compound.

Polyester urethane-containing molding compositions are described in U.S. Pat. No. 4,287,116. Briefly, an ethylenically unsaturated monomer solution having dissolved therein a polyester urethane resin and an organic polyol polyurethane precursor is gelled by the addition of a polyisocyanate polyurethane precursor. The gelled mixture then is molded and cured by copolymerization of the ethylenically unsaturated monomer and the resin. The resin typically is a condensation product of a dihydroxy-terminated poly(oxyalkylene) bisphenol A maleate or fumarate and a polyisocyanate which is further reacted with a hydroxy-terminated ester of acrylic or methacrylic acid. The polyol precursor is a saturated aliphatic polyol or alkoxylated derivative thereof. The ethylenically unsaturated monomer can be, by way of illustration, styrene, vinyltoluene, divinylbenzene, esters of acrylic or methacrylic acid, vinyl acetate, divinyl ether, and the like. Finally, the polyisocyanate precursor is an aliphatic, cycloaliphatic, or aromatic compound having at least two isocyanate groups.

U.S. Pat. No. 4,480,079 discloses molded plastic products which are produced by the in-mold copolymerization of methyl methacrylate with a polyurethane acrylate or methacrylate. The latter material is derived from a hydroxyalkyl acrylate or methacrylate by reaction of the hydroxy groups thereof with the isocyanate groups of either a polyisocyanate free of urethane groups and having an isocyanate functionality greater than two or a urethane polyisocyanate having an isocyanate functionality greater than two and derived from a polyisocyanate by reaction thereof with the hydroxy groups of an aliphatic alcohol having up to three hydroxy groups.

Some additional references are known which appear to relate to interpenetrating polymer networks. Consequently, such references will be noted herein without comments. The references are U.S. Pat. Nos. 4,359,558, 4,408,023, 4,424,305, 4,439,583, 4,439,584, 4,439,585, 4,454,309, 4,490,423, 4,496,535, and 4,551,486, U.K. Patent Application No. GB 2,150,938A, and European Patent Application No. 85105252.2, published as No. 0,163,150.

Acrylic monomers containing carbamate (urethane) functionality are described in U.S. Pat. Nos. 3,297,745, 3,425,988, 4,129,667, and 4,279,833. An acrylic monomer containing isocyanate functionality, isocyanatoethyl methacrylate, is described in *Adhesives Age,* October, 1984. The article summarizes three areas in which isocyanatoethyl methacrylate has been used: (1) applications where the methacrylate group is polymerized first, leaving the isocyanate group for a later reaction, (2) applications where the isocyanate group is reacted with a polyfunctional material first, leaving the vinyl group for a later reaction, and (3) applications where the isocyanate group is reacted with a monofunctional reagent first to make a new monomer which can be polymerized later.

Mention may be made at this point of an alternative method of achieving increased water absorbency, namely, the physical incorporation of a superabsorbent material into a polyurethane foam. This approach is illustrated by U.S. Pat. No. 3,900,030 which describes a polyurethane foam of approximately the same type as those disclosed in U.S. Pat. No. 3,903,232 et. seq. which has dispersed throughout the foam a particulate, water-swellable polymer containing a plurality of hydrophilic groups such as carboxy, carboxamide, sulfonate salt, or hydroxy groups. The particulate polymer is included to increase the water absorbency of the foam.

The use as a starting material of what may be termed polyether polyols, polyglycolethers, poly(oxyalkylene) polyols or glycols, or poly(alkyleneoxy) polyols or glycols has been studied extensively. One of the earliest references describing such materials is U.S. Pat. No. 2,948,691. According to this patent, polyglycolethers having a molecular weight of at least 500 and at least two terminal hydroxy groups can be reacted with mono- or polyfunctional isocyanates to give products which may be used for producing plasticizers, lubricants, plastics, spongy materials, gel formers, thickening agents, and the like. The patent describes the preparation of hydrogels and foams.

Subsequent studies with these poly(alkyleneoxy) polyols demonstrated a high suitability for the preparation of hydrogels and foams having particular properties, as illustrated by the references described below.

U.S. Pat. No. 3,861,993 describes a composite foam scouring pad, one component of which is a hydrophilic foam composition prepared by reacting an isocyanate-capped poly(oxyethylene) polyol having an isocyanate functionality of at least two with an aqueous solution containing a blowing agent such as a polyisocyanate, a nonionic surfactant, and, when the isocyanate-capped poly(oxyethylene) polyol isocyanate functionality is about two, a crosslinking agent. The ratio of moles of water to moles of isocyanate functionality in the polyol can range from about 6.5 to about 390. The same hydrophilic foam is employed to prepare a laminated fabric as described in U.S. Pat. No. 3,874,964 and a horticultural foam structure as described in U.S. Patent No. 3,889,417. The reticulated crosslinked polyurethane foam described in U.S. Pat. No. 3,890,254 appears to differ from that described above in that particular types of surfactants are required and the isocyanate-capped poly(oxyethylene) polyol is derived from a poly(oxyethylene) polyol having a weight average molecular weight of from about 200 to about 20,000 and a hydroxy group functionality of from about 2 to about 8. See also U.S. Pat. No. 4,160,076.

Compressed foams which are restored to their original volume in the presence of water or heat are disclosed in U.S. Pat. No. 3,903,232; see also U.S. Pat. No. 3,854,535. The foams are similar to those described in U.S. Pat. No. 3,861,993. Briefly, a moisture of from 0 to about 97 percent by weight of an isocyanate-capped hydrophilic poly(oxyethylene) polyol having an isocyanate functionality of two and an isocyanate-capped poly(oxyethylene) polyol having an isocyanate functionality of from about 3 to about 8 and a weight average molecular weight of from about 200 to about 1,500 (20,000 according to claim 1) is reacted with water, optionally in the presence of a crosslinking agent. The ratio of moles of water to moles of isocyanate groups can range from about 6.5 to about 390. See also U.S. Pat. Nos. 4,156,592 and 4,292,412 which disclose the use of such foams in the preparation of expandable fabric softener-containing articles and hydrophilic fabric softener foam compositions, respectively. Similar foams are disclosed in U.S. Pat. No. 4,110,508 and 4,137,200 in which the poly(oxyethylene) polyol moiety of the isocyanate-capped polyol has a weight average molecular weight of from about 200 to about 20,000. See also U.S. Pat. Nos. 4,201,846, 4,258,137, and 4,309,509 which describe the incorporation into the foam of U.S. Pat. No. 4,137,200 hydrophilic fibers prepared from vinyl alcohol homopolymers and copolymers, an epoxy resin, and an odorant, respectively. In addition, U.S. Pat. No. 4,127,516 describes the inclusion of a polyurea in the reaction mixture which yields the foams of U.S. Pat. No. 4,110,508. The polyurea is prepared by, for example, the reaction between a linear poly(oxyethylene) polyol which has been capped with a polyisocyanate and a polyamine in an organic solvent.

U.S. Pat. No. 3,904,557 describes a method for producing a multicolored polyurethane sponge. A poly(oxyethylene) polyol having a weight average molecular weight of from about 200 to about 20,000 and hydroxy functionality of from about 2 to about 8 is capped with a polyisocyanate. At least two distinctly different coloring agents are added to at least two different portions of isocyanate-capped polyol or water. The colored portions then are reacted with separate portions of water or isocyanate-capped polyol, respectively, to form separate colored foaming masses which then are mixed together under laminar flow conditions to yield a multicolored variegated polyurethane foam.

A polyurethane hydrogel is described in U.S. Pat. No. 4,118,354. The hydrogel is produced by dispersing into an aqueous liquid phase a product obtained by the reaction of a polyisocyanate having at least two isocyanate groups with a polyether. The polyether results from the polycondensation of at least two alkylene oxides with a polyalcohol having at least two hydroxy groups and has an average molecular weight per hydroxy group of from 1,000 to 4,000. Preferable, 75 to 85 percent of the alkylene oxides is ethylene oxide. The resulting hydrogel has a greater water content and is highly elastic and highly stable, even in the presence of a corrosive electrolyte solution.

Urethane foams having low resiliency are described in U.S. Pat. No. 4,158,087. The foams are obtained by reacting a poly(oxyalkylene) urethane prepolymer containing at least 40 mole percent of oxyethylene units in the oxyalkylene portion of the prepolymer, water, and from about 40 to about 150 parts by weight on a solids basis per 100 parts by weight of the prepolymer of a synthetic polymer latex. The prepolymer is an isocyanate-capped poly(oxyethylene) polyol of the type described in U.S. Pat. Nos. 3,903,232 et. seq.

U.S. Pat. No. 4,181,770 describes the preparation of a hydrophilic foam from an isocyanate-terminated branched polyethylene polyol, an isocyanate-terminated polyester prepolymer, a minor amount of 4,4'-diphenylmethanediisocyanate/polycarbodiimide liquid condensation product which has 30 percent free isocyanate groups, and water. The foam is stated to have improved firmness and scuff resistance properties.

Isocyanate-capped urethane-containing prepolymers prepared from polyols obtained from an epihalohydrin are described in U.S. Pat. Nos. 4,273,913 and 4,297,482. The polyol can be, for example, a polyalkylene glycol composed of the same or different oxyalkylene units or a mixture of different polyalkylene glycols.

U.S. Pat. Nos. 4,314,034, 4,365,025, 4,377,645, 4,384,050, and 4,384,051 describe variations of a general concept which involves mixing a resin phase and an aqueous phase. The resin phase comprises an isocyanate-capped poly(oxyalkylene) glycol of the type described in U.S. Pat. No. 3,903,232 et seq. and diphenylmethane diisocyanate and/or polymeric forms or isocyanate containing derivatives thereof.

While extensive research has been carried out on the preparation of polyurethane foams and superabsorbents, relatively few polyurethane foams containing a plurality of carboxylic acid groups are known. In fact, it generally is recognized that such foams are difficult to prepare; note the statement in U.S. Pat. No. 3,412,054, discussed supra. Moreover, the superabsorbent polyurethane art seems to be devoid of teachings regarding wicking rates.

SUMMARY OF THE INVENTION

During research directed to superabsorbent polyurethane foams, a class of carboxylic acid group-containing crosslinked polyurethane foams was discovered which, while not superabsorbent, unexpectedly demonstrated superior wicking properties.

Consequently, it is an object of the present invention to provide a novel class of crosslinked polyurethane foam compositions.

A further object of the present invention is to provide a novel class of crosslinked polyurethane foam compositions which contain a plurality of carboxylic acid groups.

Yet another object of the present invention is to provide a novel class of crosslinked polyurethane foam compositions which contain a plurality of carboxylic acid groups and exhibit superior wicking properties.

These other objects will be apparent to those having ordinary skill in the art from a reading of the specification and claims which follow.

Accordingly, the present invention provides an absorbent superwicking crosslinked polyurethane foam composition having incorporated therein an effective amount of at least one amino acid, a one percent by weight solution of which has a pH of no more than about 8, said amino acid containing one amino group and at least one carboxylic acid group.

In preferred embodiments, the amino acid is glycine, p-amino-benzoic acid, or an amino acid which contains two or more carboxylic acid groups and has a $pK_{A1}$ of the free acid of less than about 7. Preferred amino acids having two or more carboxylic acid groups are the monopotassium salt of glutamic acid and the monopotassium salt of aspartic acid.

The present invention also provides a method of preparing an absorbent superwicking crosslinked polyurethane foam composition which comprises mixing an isocyanate-capped prepolymer having an isocyanate functionality greater than two with an aqueous solution containing an effective amount of at least one amino acid, a one percent solution of which has a pH of less than about 8, said amino acid containing one amino group and at least one carboxylic acid group.

The present invention further provides an absorbent composite structure, at least a portion of which is composed of the superwicking crosslinked polyurethane foam composition of the present invention.

DETAILED DESCRIPTION OF THE INVENTION

The nature of the polyurethane is not known to be critical. Thus, the polyurethane can contain other polymeric moieties, such as polyesters, polyethers, and the like. However, the polyurethane must be crosslinked in order to assure foam integrity. Because of the wide variety of polyurethanes coming within the spirit and scope of the present invention which can be prepared, it is not practical to define herein precise ranges for the degree of crosslinking which will result in suitable foams. However, one having ordinary skill in the art can readily prepare foams coming within the scope of the present invention, without the need for undue experimentation, by following the guidelines contained herein.

As a practical matter, crosslinked polyurethane foams prepared from a poly(alkyleneoxy) polyol are preferred, largely because of the water miscibility and ready commercial availability of such polyols and the generally acceptable properties of the resulting foams. Especially useful are the isocyanate-capped polyurethane prepolymers which are based on such polyols, such as the HYPOL ® prepolymers available from W. R. Grace & Co., Organic Chemicals Division, Lexington, Mass.

For convenience, the term "precursor" will be used herein to mean the polyol whereas the term "prepolymer" will refer to the isocyanate-capped polyol.

In general, the amino acid can be any organic compound containing one amino group and at least one carboxylic acid group, with the proviso that a one percent by weight aqueous solution of the amino acid has a pH of no more than about 8. Thus, the amino acid can be aliphatic, cycloaliphatic, aromatic, or heterocyclic. The aliphatic and aromatic amino acids are preferred, with aliphatic amino acids being more preferred.

As used herein, the term "carboxylic acid group" is meant to include both the free acid, i.e., the —COOH group, and alkali metal salts of the acid, i.e., the —COOM group in which M is an alkali metal.

Among the aliphatic amino acids, a preferred class of compounds consists of those amino acids having one amino group and two or more carboxylic acid groups and a $pK_{A1}$ of the free acid of less than about 7. Of these, a more preferred class of amino acids is represented by the following general formula:

in which $R_1$, $R_2$, $R_3$, and $R_4$ are monovalent groups independently selected from the group consisting of hydrogen, hydroxy, carboxy, and mercapto; $M_1$ and $M_2$ independently are selected from the group consisting of hydrogen and an alkali metal, with the proviso that both $M_1$ and $M_2$ cannot be an alkali metal; m is an integer from one to three; n is an integer from zero the three; and the sum of m plus n is equal to less than five. More preferably, each of $R_1$, $R_2$, $R_3$ and $R_4$ is hydrogen; m is one or two; and n is zero. The most preferred compounds are the monopotassium salt of glutamic acid and the monopotassium salt of aspartic acid.

In general, the superwicking crosslinked polyurethane foams of the present invention can be prepared by any of the methods known to those having ordinary skill in the art. For example, one or more suitable polyol precursors, one or more suitable polyisocyanates (or polyisothiocyanates), water, and one or more amino acids can be mixed to give a superwicking crosslinked polyurethane foam. If desired, the mixture also can contain surfactants; fillers; stabilizers; additives, such as flame retardants, reinforcing agents, auxiliary blowing agents, medicaments, fragrances, colorants, cleaners, and abrasives; and the like. Preferably, all such surfactants, fillers, stabilizers, additives, and the like will be substantially nonreactive with isocyanate, hydroxy, and amine groups under the conditions of foam formation.

By way of illustration only, suitable polyisocyanates and polyisothiocyanates which can be employed include polyaryl polyisocyanates such as those described in U.S. Pat. No. 2,683,730, toluene-2,4-diisocyanate, toluene-2,6-diisocyanate, ethylidene diisocyanate, propylene-1,2-diisocyanate, cyclohexylene-1,2-diisocyanate, cyclohexylene-1,4-diisocyanate, triphenylmethane-4,4',4''-triisocyanate, m-phenylene diisocyanate, 4,4'-biphenylene diisocyanate, 3,3'-dichloro-4,4'-biphenylene diisocyanate, benzene-1,3,5-triisocyanate, toluene-2,4,6-triisocyanate, diphenyl-2,4,4'-triisocyanate, 1,4-tetramethylene diisocyanate, 1,6-hexamethylene diisocyanate, 1,10-decamethylene diisoycanate, xylene diisocyanate, chlorophenylene diisocyanate, diphenylmethane-4,4'diisocyanate, naphthalene-1,5-diisocyanate, cumene-2,4-diisocyanate, 4-methoxy-1,3- phenylene diisocyanate, 4-chloro-1,3-phenylene diisocyanate, 4-bromo-1,3-phenylene diisocyanate, 4-ethoxy-1,3-phenylene diisocyanate, 4-bromo-1,3-phenylene diisocyanate, 4-ethoxy-1,3-phenylene diisocyanate, 2,4-diisocyanatodiphenyl ether, 5,6-dimethyl-1,3-phenylene diisocyanate, 2,4-dimethyl-1,3-phenylene diisocyanate, 4,4'-diisocyanatodiphenyl ether, benzidine diisocyanate, xylene-alpha, alpha'diisothiocyanate, 3,3'-dimethyl-4,4'-biphenylene diisocyanate, 2,2',5,5'-tetramethyl-4,4'-biphenylene diisocyanate, 4,4'-methylene-bis(-phenylisocyanate), 4,4'-sulfonylbis(phenylisocyanate), 4,4'-methylene di-o-tolylisocyanate, ethylene diisocyanate, ethylene diisothiocyanate, trimethylene diisocyanate, and the like.

Alternatively, and preferably, one or more suitable isocyanate-capped polyol precursors can be mixed with water and one or more amino acids to give the foam compositions of the present invention. As before, the mixture also can contain surfactants; filters; stabilizers; additives, such as flame retardants, reinforcing agents, auxiliary blowing agents, medicaments, fragrances, colorants; cleaners and abrasives; and the like.

As already indicated, the preferred polyol precursors are poly(alkyleneoxy) polyols. More preferable, such polyols will be poly(ethyleneoxy) polyols or poly(propyleneoxy) polyols or a mixture thereof. Such polyols must have a hydroxy functionality of at least two hydroxy groups per molecule. When such hydroxy group functionality is two, it is necessary to use either an isocyanate or mixture of isocyanates having an isocyanate functionality greater than two or more crosslinking agents other than polyisocyanates in order to obtain the requisite crosslinking in the resulting polyurethane foam. When the polyols have a hydroxy functionality greater than two, the use of polyisocyanates having an isocyanate functionality greater than two or other crosslinking agents is optional.

Examples of crosslinking agents other than polyisocyanates or polyisothiocyanates include, among others, toluene-2,4,6-triamine, ethylene diamine, diethanolamine, diethylene triamine, triethylene tetramine, tetraethylene pentamine, ethanolamine, and the like.

Alternatively, such polyols can be the condensation products of one or more polyhydroxy compounds with a mixture of, for example, ethylene oxide and propylene oxide. The polyhydroxy compounds will have at least two hydroxy groups per molecule. If two or more polyhydroxy compounds are employed, all of such compounds can be diols, in which case one or more crosslinking agents must be employed. As already noted, the crosslinking agent can be a polyisocyanate having an isocyanate functionality greater than two.

On the other hand, the mixture of two or more polyhydroxy compounds can include diols and polyols having three or more hydroxy groups per molecule. Under such circumstances, the polyisocyanate can be a diisocyanate and the use of a crosslinking agent becomes optional.

In a manner which is analogous to the use of polyols per se, the isocyanate-capped prepolymers must have an isocyanate functionality of at least two. When such isocyanate functionality is two, one or more crosslinking agents must be employed. When such isocyanate functionality is greater than two, the use of crosslinking agents becomes optional.

Preferably, the isocyanate functionality of the isocyanate capped prepolymers will be greater than two and more preferably at least about 2.3. Similarly, when polyol precursors are employed, the hydroxy group functionality of the polyols or the isocyanate functionality of the polyisocyanates used preferably will be at least about 2.3.

The reaction conditions for foam generation are not known to be critical. However, when the amino acids employed consist of one or more compounds having an amino group and two or more carboxylic acid groups, at least one of which is present as an alkali metal salt, the reaction temperature preferably is maintained at or below about 40 degrees C. At temperatures greater than about 40 degrees C., foam stability may be impaired. This moderation of the reaction temperature, though, is not required for an amino acids coming within this group. For example, as will be seen in the examples, the use of such temperature moderation was not required for potassium glutamate, but was necessary with potassium aspartate.

Temperature control, when either desired or necessary, can be accomplished by any known means. A particularly useful method involves simply cooling one or more of the reactants. In general, sufficient cooling can be accomplished by cooling only the aqueous phase.

As a general rule, the amino acids to be incorporated into the crosslinked polyurethane foams will be dissolved in the aqueous phase. The aqueous phase also can contain surfactants and other materials as is well known in the art.

While not required, the use of one or more surfactant is preferred. The presence of a surfactant contributes to smaller and more uniform cells in the foam, but is not known to significantly contribute to the wicking properties of the foam compositions. The choice of surfactant and the amount employed are variables which are well known to those having ordinary skill in the art. However, nonionic surfactants are preferred in order to avoid potential ionic interactions with the amino acids which may lead to precipitation of the amino acids or inactivation of the amino acid carboxylate functionality. In addition, ionic surfactants may react with the isocyanate groups which are present in the reaction mixture, thereby decreasing total isocyanate functionality and/or inactivating the surfactant.

The amounts of isocyanate-capped prepolymer or polyol precursor and polyisocyanate, water, amino acids, and surfactant, if employed, which can be used are readily determined by those having ordinary skill in the art. As a general rule, suitable foams are obtained when the isocyanate-capped prepolymer or polyol precursor and polyisocyanate phase and the aqueous phase containing amino acids and surfactant, if used, are mixed in approximately equal parts by weight.

The present invention is further described by the following examples which illustrate preferred embodiments. Such examples are not to be construed as in any way limiting either the spirit or scope of the present invention. In the examples, all temperatures are in degrees Celsius and all amounts are in parts by weight, unless specified otherwise.

EXAMPLE 1

A one percent solution of the monopotassium salt of glutamic acid in water was prepared. The pH of the solution at 25 degrees was 7.08. Equal parts of this aqueous glutamic acid solution and an isocyanate-capped poly(alkyleneoxy) polyol were mixed at ambient temperature in a Hamilton Beach Model No. 936 Drink Mixer (Scovil, Inc., Hamilton Beach Division, Waterbury, Conn.). The resulting mixture was poured into a tray and allowed to cure. The foam obtained was very absorbent and appeared to have excellent water retention. The isocyanate-capped polyol was HYPOL® FHP 2002 (W. R. Grace & Co., Organic Chemicals Division, Lexington, Mass.). The material is reported to have a molecular weight of 1,400, an isocyanate functionality of 2.3, and a total isocyanate group content of 1.6 meg/g with 0.3 percent free toluene diisocyanate, the polyisocyanate employed to cap the polyol.

EXAMPLE 2

The procedure of Example 1 was repeated, except that a one percent aqueous solution of the monopotassium salt of aspartic acid was employed. Such solution had a pH of 6.78. The foam obtained was similar in appearance to foams made without any amino acid in the aqueous phase.

EXAMPLE 3

The procedure of Example 1 was repeated, except that a one percent aqueous solution of glycine was employed. The solution had a pH of 6.67. The foam obtained was soft, absorbent, and fine-celled.

EXAMPLE 4

The procedure of Example 1 was repeated, except that a one percent aqueous solution of aspartic acid was employed. The solution had a pH of 2.98. Except for a little finer cell structure, the foam obtained was similar in appearance to that obtained in the absence of amino acid.

EXAMPLE 5

The procedure of Example 1 was repeated, except that a saturated aqueous solution of p-aminobenzoic acid was used. The solution appeared to contain less than one percent solute and had a pH of 3.73. Except for a finer cell structure, the foam obtained was similar in appearance to that obtained in the absence of amino acid.

EXAMPLE 6

In order to study the relationship of reaction temperature to foam formation, the procedure of Example 1 was repeated, except that the aqueous solution contained five percent of the monopotassium salt of glutamic acid. The solution was divided into four equal portions, one of which was maintained at ambient temperature (25 degrees). The other three portions were cooled to different temperatures. A fifth, control portion consisted of water only at ambient temperature. Foams were prepared as described in Example 1. The maximum temperature reached during the foaming reaction was recorded. The temperature data are summarized in Table 1.

TABLE 1

| Sample | Summary of Aqueous Phase and Maximum Reaction Temperatures | |
|---|---|---|
|  | Temperature Amino Acid Sol'n | Maximum Reaction Temperature |
| Control | 25 | 40 |
| A | 25 | 56.6 |
| B | 15 | 44.0 |
| C | 10 | 44.5 |
| D | 7 | 38.0 |

Upon standing, the foam from Sample A collapsed and the foams from Sample B and C were partially collapsed. The control foam and the foam obtained from Sample D were of approximately similar appearance and of good quality.

These data suggest that, at least with some amino acids, the reaction temperature during the foaming reaction should not exceed about 40 degrees.

EXAMPLE 7

The procedure of Example 6 was repeated, except that aqueous solutions containing varying amounts of the monopotassium salt of glutamic acid were employed. Four solutions were prepared which contained 2.5, 5.0, 7.5, and 10.0 percent potassium glutamate, respectively. The solutions were cooled to 0–7 degrees. Very nice foams were obtained with the 2.5 and 5.0 percent solutions. Good foam quality was obtained with the other two solutions only upon cooling the solutions to about 2 degrees and carrying out the foaming reaction in a vessel which was cooled in an ice bath.

Under the conditions of this esperiment, 10 percent appears to be an approximate upper limit for the amino acid. It should be kept in mind, however, that changing the nature and/or the amount of the isocyanate-capped prepolymer and using a different amino acid probably will affect the maximum amount of the amino acid which can be incorporated into the polyurethane foam.

EXAMPLE 8

In the experiments carried out thus far, no attemps had been made to evaluate the simple observation that the foams prepared in accordance with the present invention appeared to have wicking properties which were superior to those of foams prepared without amino acids. Accordingly, a series of foams were prepared with the intent to obtain a quantitative evaluation of wicking properties. The foams were prepared as described in preceding examples. All solutions containing potassium glutamate were cooled to 0–10 degrees before carrying out the foaming reaction. In addition, half of the samples also contained a surfactant at a level of 0.25 percent. The surfactant was Pluronic F68, a block copolymer of ethylene oxide and propylene oxide at a 5:1 molar ratio and had a molecular weight of 8400 (BASF Wyandotte Corporation, Parsippany, N.J.). The aqueous solutions which were used are summarized in Table 2.

TABLE 2

| Sample | Summary of Aqueous Phase Compositions | | |
|---|---|---|---|
|  | Amino Acid | Percent | Surfactant |
| A | Potassium glutamate | 2.5 | No |
| B | Potassium glutamate | 5.0 | No |
| C | Potassium glutamate | 6.0 | No |
| D | Potassium glutamate | 2.5 | Yes |
| E | Potassium glutamate | 5.0 | Yes |
| F | Potassium glutamate | 6.0 | Yes |
| G | Glycine | 2.5 | No |
| H | Glycine | 5.0 | No |
| I | Glycine | 10.0 | No |
| J | Glycine | 2.5 | Yes |
| K | Glycine | 5.0 | Yes |
| L | Glycine | 10.0 | Yes |

In every case, the resulting foams were of good quality. Cell structures, however, were not uniform from sample to sample. Consequently, it was felt that the wicking studies needed to be carried out on samples having reasonably uniform cell structures in order to eliminate cell structure as a significant variable in such studies.

EXAMPLE 9

The procedure of Example 8 was repeated, except that varying amounts of the surfactant were employed with two different amino acids. The compositions of the aqueous phases are summarized in Table 3 which follows.

TABLE 3

Summary of Aqueous Phase Compositions

| Sample | Amino Acid | Amt., g | F68, g | H₂O, g |
|---|---|---|---|---|
| A | — | — | — | 100 |
| B | — | — | 0.50 | 99.5 |
| C | — | — | 1.50 | 98.5 |
| D | Potassium glutamate | 10.0 | — | 89.5 |
| E | Potassium glutamate | 10.0 | 0.50 | 89.5 |
| F | Potassium glutamate | 10.0 | 1.50 | 89.5 |
| G | Potassium aspartate | 10.0 | — | 89.5 |
| H | Potassium aspartate | 10.0 | 0.50 | 89.5 |
| I | Potassium aspartate | 10.0 | 1.50 | 89.5 |

The surfactant, when used, and the amino acid, when used, were dissolved in the water. The aqueous potassium glutamate solutions were cooled to 0–5 degrees before mixing with the prepolymer. In each case, the amount of prepolymer used was 100 g.

The foams obtained in the presence of surfactant clearly resulted in a softer foam having a finer cell structure. This result was independent of the presence of amino acid. With the potassium aspartate foams, there appeared to be little difference between the two levels of surfactant. With the potassium glutamate foams, however, the lower level (0.25 percent) of surfactant gave clearly superior appearing foams; the higher level (0.75 percent) of surfactant gave a mushy, sticky foam. Based on the results of this example, a level of 0.25 percent was chosen as the level to be used for the preparation of foams for wicking rate studies.

EXAMPLE 10

Because foams containing higher levels of potassium aspartate have not been satisfactory, two foams were prepared with 0.25 percent of Igepal CO-430, a p-nonylphenol ethoxylate having four ethylene oxide units (GAF Corporation, Linden, N.J. The levels of amino acid were 5.0 and 7.0 percent, respectively. While some improvement was seen, the foams still were unsatisfactory.

EXAMPLE 11

Adhesion between the foam and the mold and skin formation at the mold-foam interface have been ongoing problems. The use of Teflon ®-coated molds and coating mold surfaces with silicone did not help. Coating the mold with glycerine also failed to prevent the problems. However, spraying the model with PAM ®, a household nonstick cooking agent, caused the mold to readily release the foam and prevented skin formation.

EXAMPLE 12

Foam samples were prepared for demand absorbency testing as already described in previous examples (especially Example 9). In every case, the aqueous phase contained 0.25 percent Pluronic F68. The amino acid compositions of the aqueous phases are summarized in Table 4 below.

TABLE 4

Summary of the Amino Acid Compositions of the Aqueous Phases

| Sample | Amino Acid | Percent |
|---|---|---|
| A | Potassium glutamate | 7.0 |
| B | Potassium glutamate | 5.0 |
| C | Potassium glutamate | 2.5 |
| D | Glycine | 7.0 |
| E | Glycine | 5.0 |
| F | Glycine | 2.5 |
| G | Potassium aspartate | 2.5 |
| H[a] | — | — |

[a]Control

All of the foams had cell structures which were reasonably consistent with that of the control foam, Sample H.

To carry out the demand absorbency test, three-inch (7.6-cm) diameter portions of foam were cut from each sample; the foam was approximately ¼ inch (6 mm) thick. The test procedure employed 0.9 percent aqueous sodium chloride at a pressure of 0.1 p.s.i.g. Sample weights were obtained every 5 sec with a Model 3006 Arbor Electronic Balance which was interfaced with a computer to automate the weighings over time and to process the data. The computer hardware consisted of a Model 515040 IBM Personal Computer, Feature No. 1504900 IBM Monochrome Display and Printer Adapter, Model No. 5151001 IBM Monochrome Display, IBM Disc Drive, and an AST 256KB Mega and Memory Board with Clock. Other equipment included an Epson MX100 Matrix Printer, a Color Graphics Adapter Board, Color Graphics Monitor, and Interface Models 7077 (balance) and ZT1488 (computer). Data processing and graphing were done with Lotus 1-2-3 software.

The results of the demand absorbency test are summarized in Table 5 (although the test generated data points every five seconds, the table presents the data for readings at 30-second intervals in order to conserve space):

TABLE 5

Summary of the Results of the Demand Absorbency Test

| Time | Control | A | B | C | D | E | F | G |
|---|---|---|---|---|---|---|---|---|
| 30 | 0 | 4.26 | 0.19 | 0.12 | 3.51 | 3.21 | 0.33 | 2.21 |
| 60 | 0.07 | 10.46 | 0.63 | 0.30 | 7.66 | 8.55 | 0.94 | 7.06 |
| 90 | 0.09 | 15.50 | 1.34 | 0.60 | 9.92 | 11.77 | 1.91 | 11.44 |
| 120 | 0.14 | 18.84 | 2.43 | 1.03 | 11.55 | 13.56 | 3.21 | 14.69 |
| 150 | 0.13 | 20.06 | 4.07 | 1.57 | 12.44 | 14.79 | 4.50 | 16.58 |
| 180 | — | 20.37 | 6.13 | 2.29 | 13.01 | 15.67 | 5.51 | 17.77 |
| 210 | — | — | 8.94 | 3.03 | 13.43 | 16.36 | 6.24 | 18.65 |
| 240 | — | — | 11.04 | 3.81 | 13.73 | 16.81 | 6.74 | 19.33 |
| 270 | — | — | 12.86 | 4.48 | 13.93 | 17.15 | 7.24 | 19.91 |
| 300 | — | — | 14.52 | 5.13 | 14.08 | 17.43 | 7.59 | 20.38 |
| 330 | — | — | 15.99 | 5.64 | 14.22 | 17.71 | 7.94 | 20.79 |
| 360 | — | — | 17.05 | 6.12 | — | 17.91 | 8.21 | 21.13 |
| 390 | — | — | 18.11 | 6.54 | — | 18.04 | 8.49 | 21.43 |
| 420 | — | — | 18.79 | 6.94 | — | 18.11 | 8.70 | 21.67 |
| 450 | — | — | 19.47 | 7.34 | — | 18.22 | 8.96 | 21.87 |
| 480 | — | — | 20.12 | 7.72 | — | — | 9.14 | 22.02 |
| 510 | — | — | 20.62 | 8.09 | — | — | 9.33 | 22.14 |
| 540 | — | — | 21.04 | 8.48 | — | — | 9.53 | 22.21 |
| 570 | — | — | 21.41 | 8.81 | — | — | 9.66 | 22.30 |
| 600 | — | — | 21.76 | 9.06 | — | — | 9.85 | 22.37 |
| 630 | — | — | 22.04 | 9.34 | — | — | 9.98 | 22.41 |
| 660 | — | — | 22.32 | 9.54 | — | — | 10.11 | — |
| 690 | — | — | 22.57 | 9.81 | — | — | 10.24 | — |
| 720 | — | — | 22.76 | 10.01 | — | — | 10.37 | — |
| 750 | — | — | 22.96 | 10.28 | — | — | 10.50 | — |
| 780 | — | — | 23.10 | 10.48 | — | — | — | — |
| 810 | — | — | — | 10.63 | — | — | — | — |
| 840 | — | — | — | 10.83 | — | — | — | — |
| 870 | — | — | — | 10.96 | — | — | — | — |

TABLE 5-continued

| | Summary of the Results of the Demand Absorbency Test | | | | | | |
|---|---|---|---|---|---|---|---|
| Time | Control | A | B | C | D | E | F | G |
| 900 | — | — | — | 11.10 | — | — | — | — |

For convenience, the absorptive capacities of the foams are summarized in Table 6, which also presents normalized values, i.e., capacities per unit weight.

TABLE 6

| | Summary of Foam Absorptive Capacities | | |
|---|---|---|---|
| Sample | Sample Wt., g | Capacity, g | Capacity per g |
| Control | 3.16 | 0.13 | 0.04 |
| A | 2.88 | 20.37 | 7.07 |
| B | 3.01 | 23.10 | 7.67 |
| C | 2.86 | 11.10 | 3.88 |
| D | 2.71 | 14.22 | 5.25 |
| E | 2.80 | 18.22 | 6.51 |
| F | 3.16 | 10.50 | 3.32 |
| G | 2.79 | 22.41 | 8.03 |

Because the various foams summarized in Table 6 contain varying amounts of amino acids, it is instructive to look at the absorptive capacities per g on the basis of unit amino acid concentration. These data are summarized in Table 7.

TABLE 7

| | Summary of Normalized Absorptive Capacities | | |
|---|---|---|---|
| Sample | Percent Amino Acid | Capacity per g | Capacity per g per % of Amino Acid |
| Control | — | 0.04 | — |
| A | 7.0 | 7.07 | 1.01 |
| B | 5.0 | 7.67 | 1.53 |
| C | 2.5 | 3.88 | 1.55 |
| D | 7.0 | 5.25 | 0.75 |
| E | 5.0 | 6.51 | 1.30 |
| F | 2.5 | 3.32 | 1.33 |
| G | 2.5 | 8.03 | 3.21 |

Figure 1:
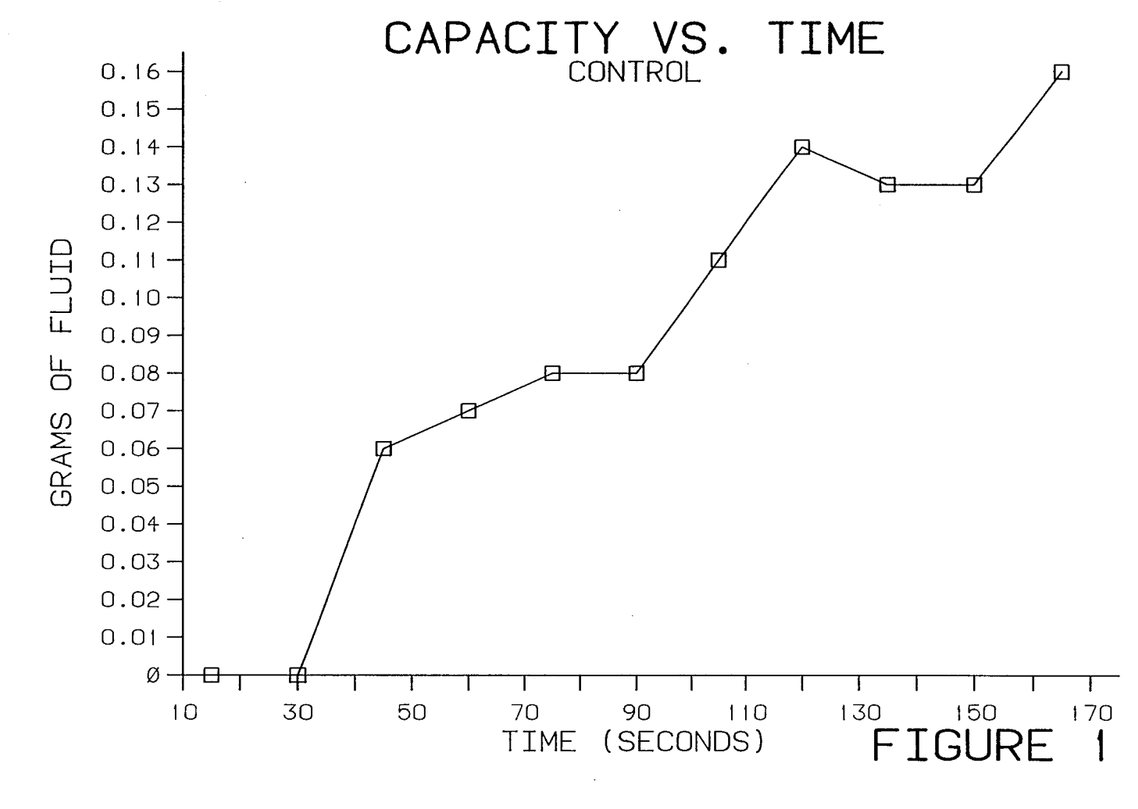
FIGS. 1-8, inclusive, are the capacity versus time curves obtained during demand absorbency tests carried out on the foams of Example 12, with FIG. 1 being the control curve.
Figure 2:
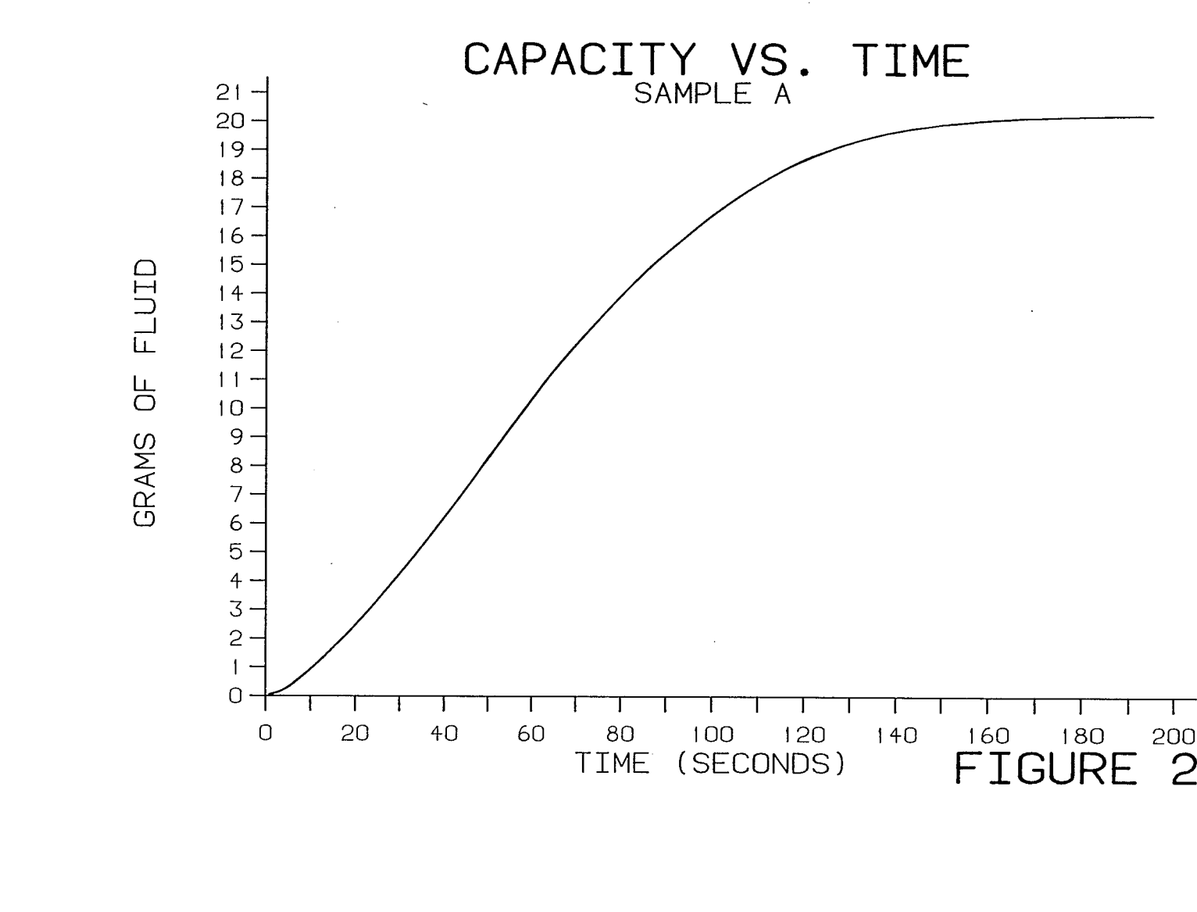
Figure 3:
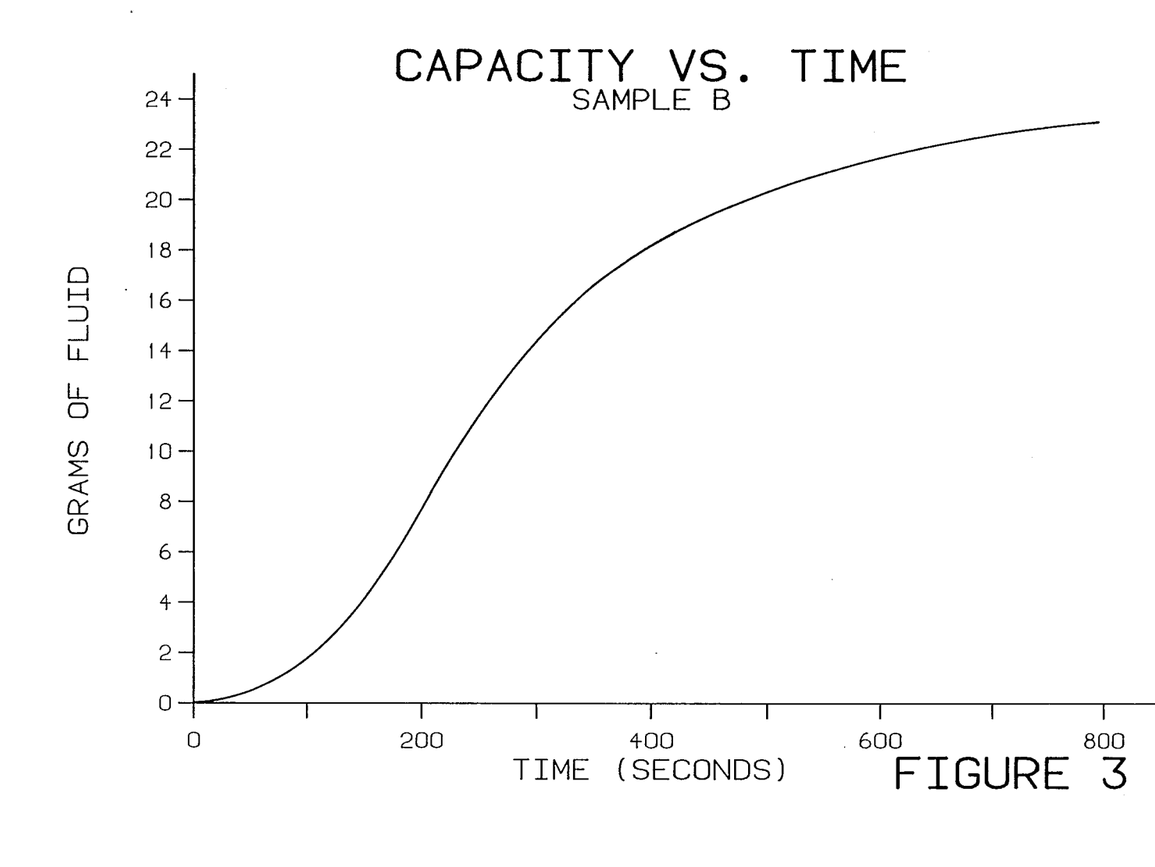
Figure 4:
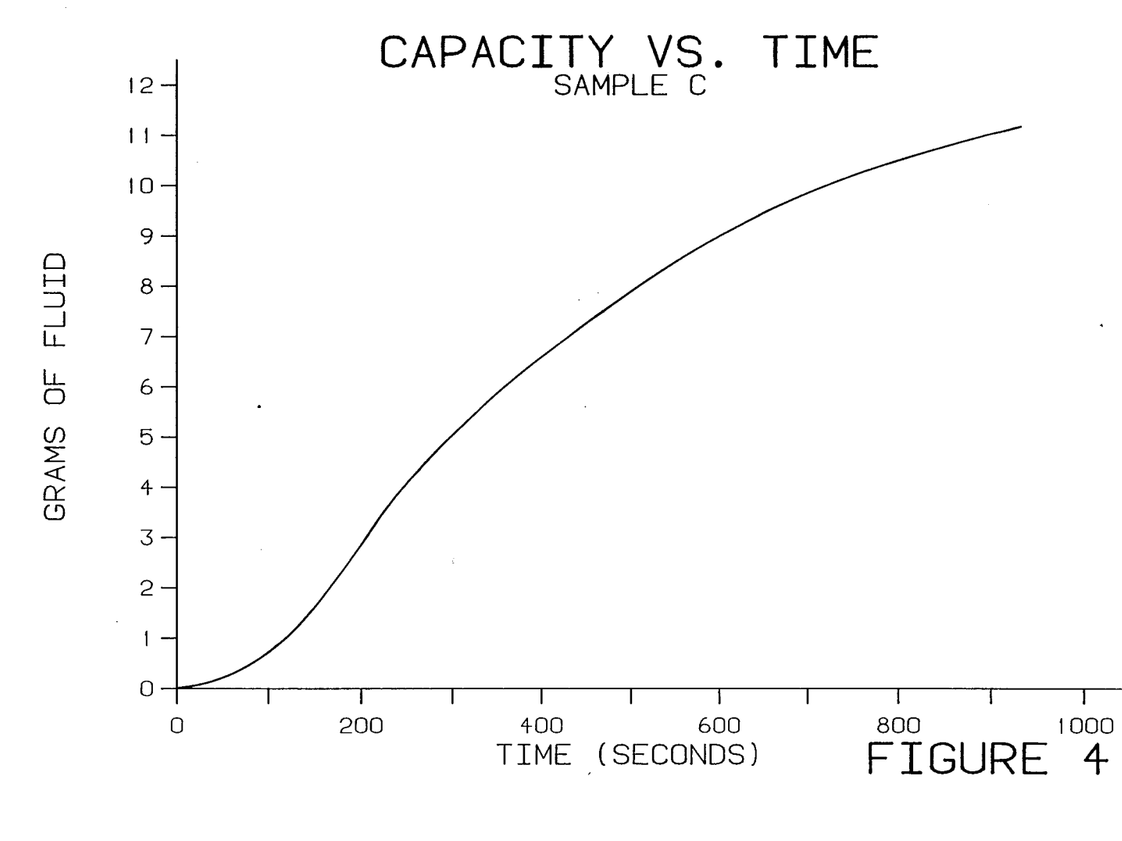
Figure 5:
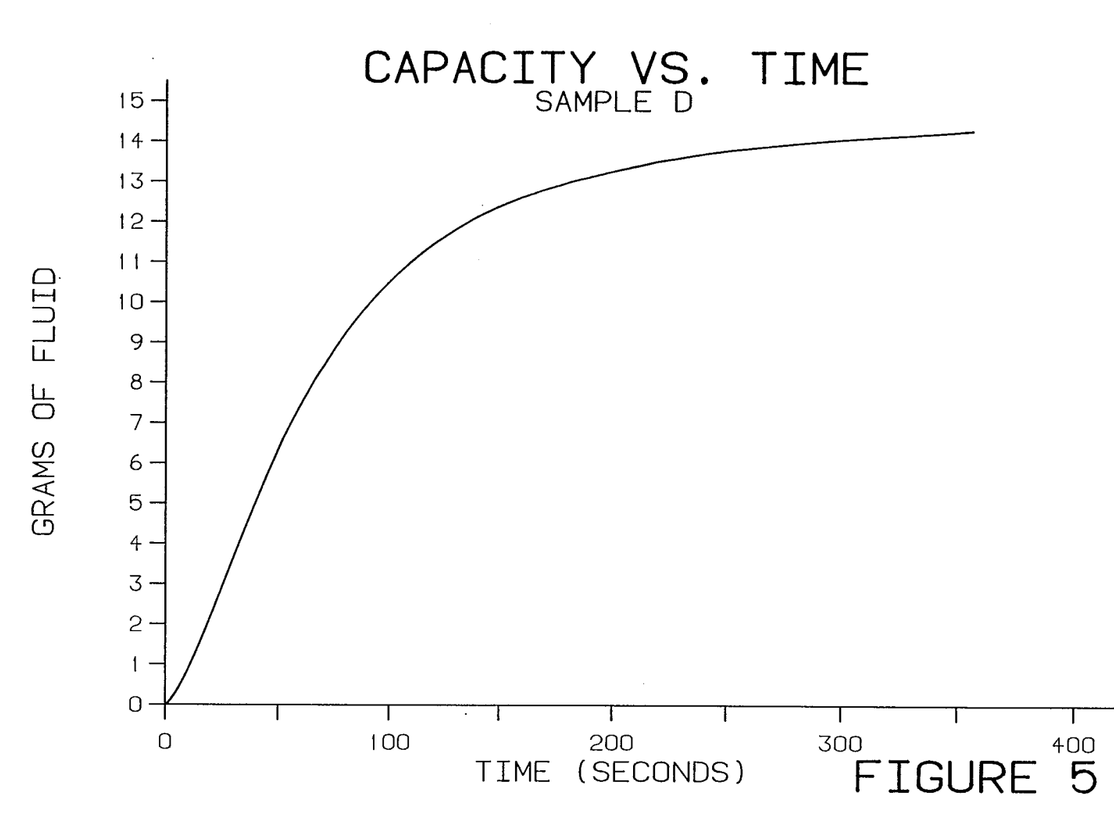
Figure 6:
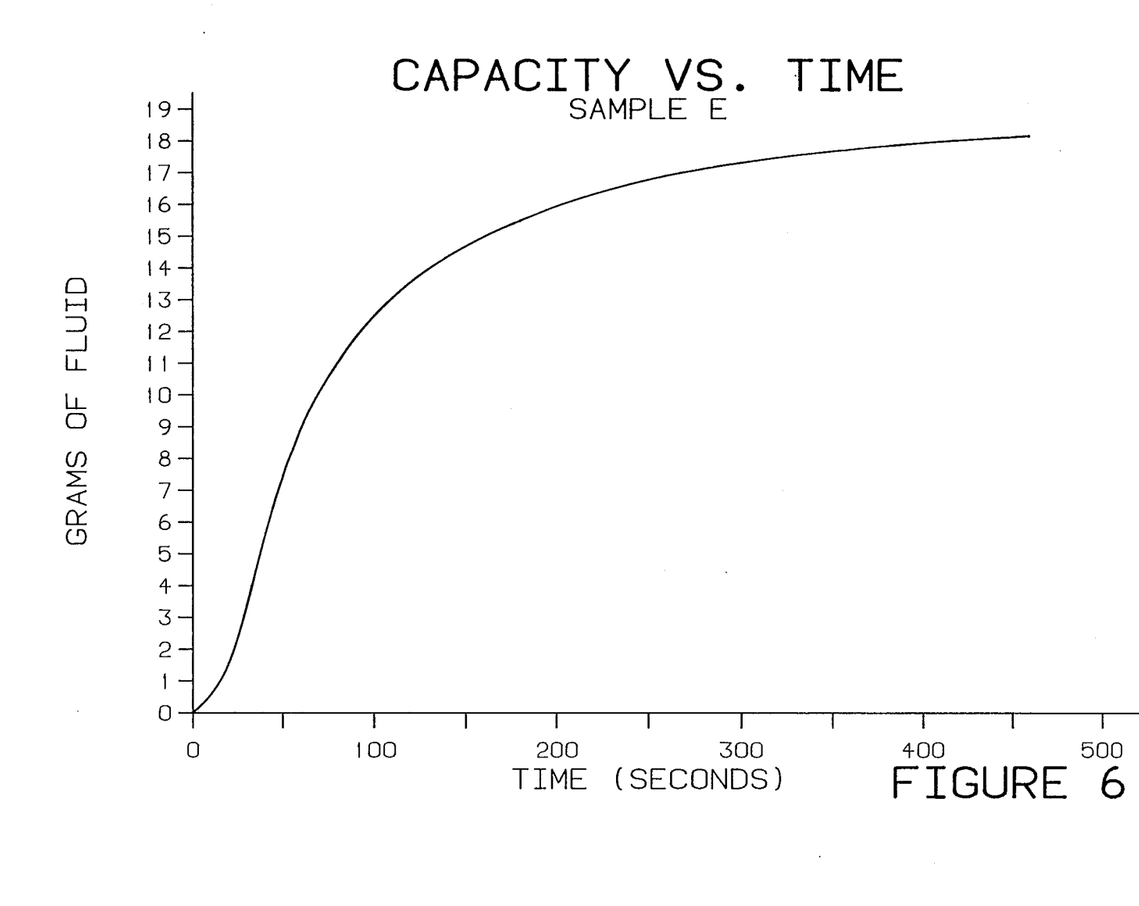
Figure 7:
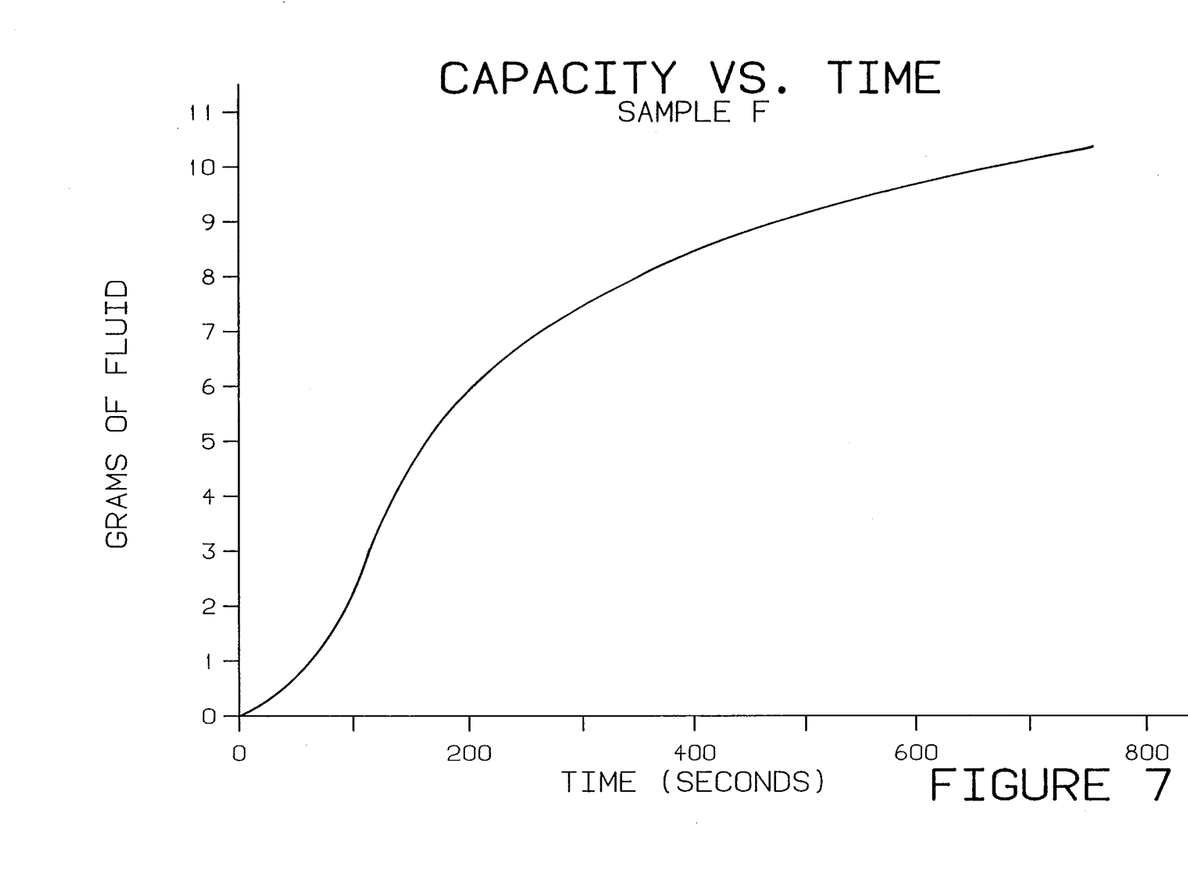
Figure 8:
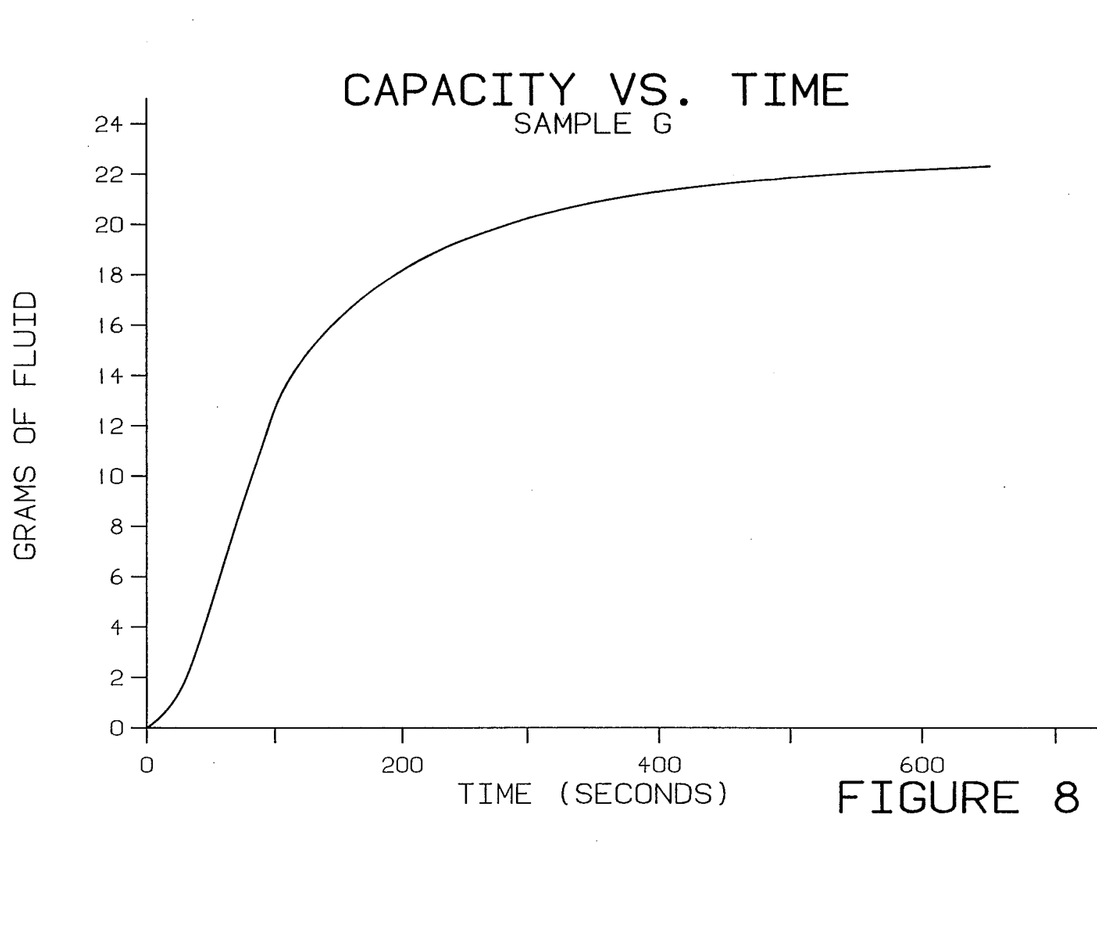

The data in Table 5, plus the data for the other readings not included therein, are shown graphically in FIGS. 1-8, inclusive. By estimating the slopes of the steepest, straight-line portions of the curves obtained, maximum absorption rates were determined. These values are summarized in Table 8.

TABLE 8

| Summary of Estimated Maximum Absorption Rates | |
|---|---|
| Sample | Estimated Maximum Absorption Rate, g per sec |
| Control | 0.001 |
| A | 0.208 |
| B | 0.079 |
| C | 0.025 |
| D | 0.170 |
| E | 0.187 |
| F | 0.042 |
| G | 0.147 |

The differences in both absorptive capabilities and absorbency rates between the foams of the present invention and the control foam are striking. Moreover, because the control foam also contains surfactant at the same level as the foams of the present invention, it is evident that the surfactant is not contributing to the remarkable increases in both absorptive capacities and absorbency rates observed as a result of including in the polyurethane foams an amino acid as taught herein. By way of illustration, the absorptive capacities of the foams of the present invention are from about 83 to about 200 times that of the control foam on a per g of foam basis and the estimated maximum absorbency rates are from about 25 to about 208 times faster, also on a per g of foam basis.

Figure 9:
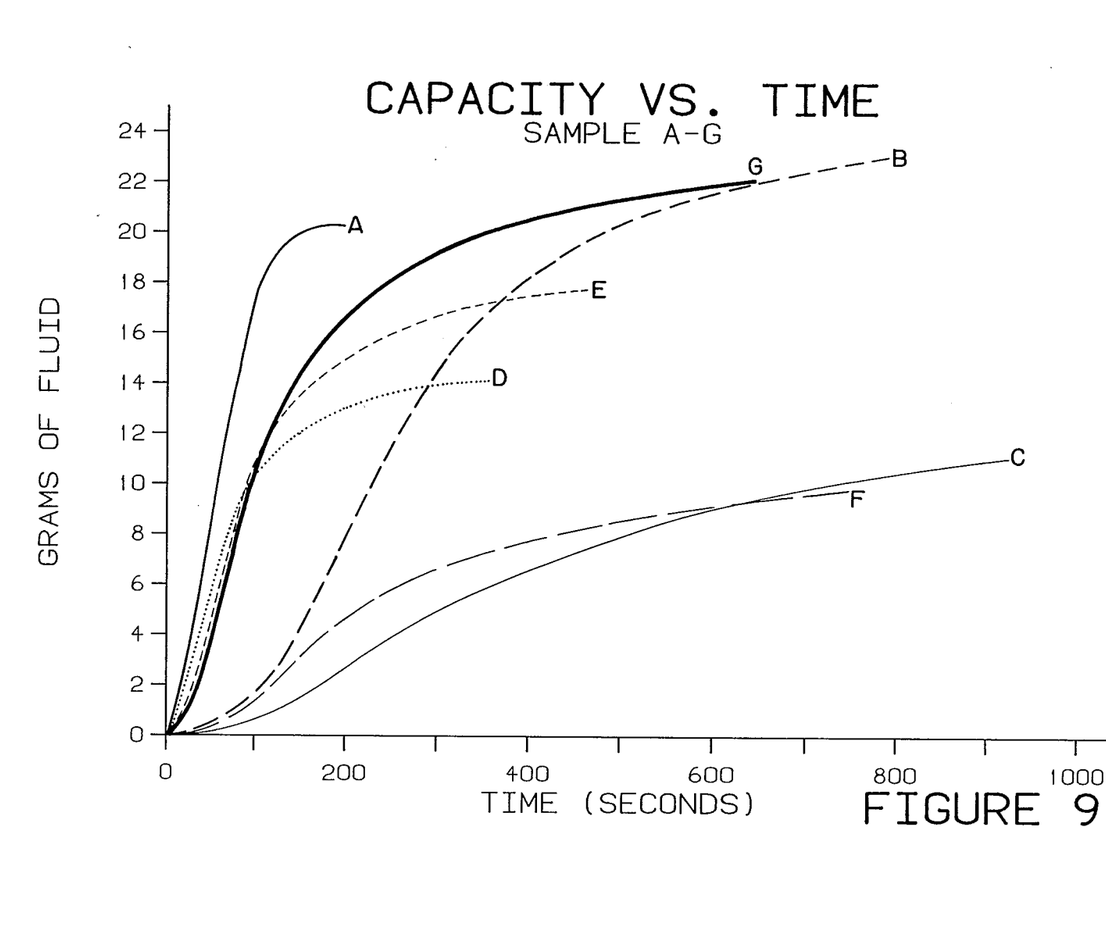
FIG. 9 shows the curves of FIGS. 2-8, inclusive, on the same graph for comparison purposes.

The data in Tables 5-8, inclusive, and the figures indicate that there are some interesting differences among the several amino acids studied. For example, the amino acid which is most effective in increasing the absorptive capacity of the foam on a per unit concentration basis is potassium aspartate. The same amino acid also gives the highest maximum absorbency rate at a level of 2.5 percent by weight. When the amino acid is glycine, there appears to be little if any differences between concentrations of 5.0 weight percent and 7.0 weight percent. When the amino acid is potassium glutamate, however, increasing the concentration in the foam from 5.0 weight percent to 7.0 weight percent causes a significant increase in the estimated maximum absorbency rate but an approximately 30 percent decrease in the absorptive capacity on a per g of foam per percent of amino acid basis.

While the superwicking crosslinked polyurethane foam compositions of the present invention are useful in their own right as absorbent articles such as sponges and the like, such foam compositions also should prove useful in the manufacture of absorbent composite structures, especially absorbent, layered composite structures such as disposable diapers, incontinent products, disposable bibs, feminine care products such as tampons and napkins, and the like.

Having thus described the invention, numerous variations and modifications will be readily apparent to those having ordinary skill in the art without departing from either the spirit or scope of the invention.

What is claimed is:

1. An absorbent superwicking crosslinked polyurethane foam composition having incorporated therein an effective amount of at least one amino acid, a one percent by weight aqueous solution of which has a pH of no more than about 8, said amino acid containing one amino group and at least one carboxylic acid group.

2. The polyurethane foam composition of claim 1, in which said amino acid is glycine.

3. The polyurethane foam composition of claim 1, in which said amino acid is p-aminobenzioc acid.

4. the polyurethane foam composition of claim 1, in which said amino acid contains two or more carboxylic acid groups and has a pKA1 of the free acid of less than about 7.

5. The polyurethane foam composition of claim 4, in which said amino acid has the general formula, in which $R_1$, $R_2$, $R_3$, and $R_4$, are monovalent groups independently selected from the group consisting of hydrogen, hydroxy, carboxy, and mercapto; $M_1$ and $M_2$ independently are selected from the group consisting of hydrogen and an alkali metal, with the proviso that both $M_1$ and $M_2$ cannot be an alkali metal, m is an integer from one to three; n is an integer from zero to three; and the sum of m plus n is equal to or less than five.

6. The polyurethane foam composition of claim 5, in which each of $R_1$, $R_2$, $R_3$, and $R_4$ is hydrogen; m is one or two; and n is zero.

7. The polyurethane foam composition of claim 6, in which said amino acid is the monopotassium salt of glutamic acid.

8. The polyurethane foam composition of claim 6, in which said amino acid is the monopotassium salt of aspartic acid.

9. A method of preparing an absorbent superwicking crosslinked polyurethane foam composition which comprises mixing an isocyanate-capped prepolymer having an isocyanate functionality greater than two with an aqueous solution containing an effective amount of at least one amino acid, a one percent by weight aqueous solution of which has a pH of less than about 8, said amino acid containing one amino group and at least one carboxylic acid group.

10. The method of claim 9, in which said prepolymer has an isocyanate funtionality of at least about 2.3.

11. The method of claim 9, in which the temperature of the reaction which results from said mixing is maintained at or below about 40 degrees C.

12. The method of claim 9, in which the aqueous solution also contains a surfactant.

13. The method of claim 9, in which said amino acid is glycine.

14. The method of claim 9, in which said amino acid is p-aminobenzoic acid.

15. The method of claim 9, in which said amino acid contains two or more carboxylic acid groups and has a pKA1 of the free acid of less than about 7.

16. The method of claim 15, in which said amino acid has the general formula, in which $R_1$, $R_2$, $R_3$, and $R_4$ are monovalent groups selected from the group consisting of hydrogen, hydroxy, carboxy, and mercapto; $M_1$ and $M_2$ independently are selected from the group consisting of hydrogen and an alkali metal, with the proviso that both $M_1$ and $M_2$ cannot be an alkali metal; m is an integer from one to three; n is an integer from zero to three; and the sum of m plus n is equal to or less than five.

17. The method of claim 16, in which said amino acid is the monopotassium salt of glutamic acid.

18. The method of claim 16, in which said amino acid is the monopotassium salt of aspartic acid.

19. An absorbent composite structure comprising an absorbent superwicking crosslinked polyurethane foam article having incorporated in said foam an effective amount of at least one amino acid, a one percent by weight aqueous solution of which has a pH of no more than about 8, said amino acid containing one amino group and at least one carboxylic acid group.

20. An absorbent, layered composite structure in which at least one layer comprises an absorbent superwicking crosslinked polyurethane foam having incorporated therein an effective amount of at least one amino acid, a one percent aqueous solution of which has a pH of no more than about 8, said amino acid containing one amino group and at least one carboxylic acid group.

* * * * *